(12) United States Patent
Duerk et al.

(10) Patent No.: US 8,111,068 B2
(45) Date of Patent: *Feb. 7, 2012

(54) REDUCING EFFECTS OF ROTATIONAL MOTION

(76) Inventors: Jeffrey L. Duerk, Avon Lake, OH (US); Ajit Shankaranarayanan, San Mateo, CA (US); Michael Wendt, Erlangen (DE); Jonathan S. Lewin, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/890,963

(22) Filed: Sep. 27, 2010

(65) Prior Publication Data

US 2011/0158477 A1 Jun. 30, 2011

Related U.S. Application Data

(63) Continuation of application No. 11/224,822, filed on Sep. 13, 2005, now Pat. No. 7,830,144, which is a continuation of application No. 10/475,382, filed on Oct. 23, 2003, now Pat. No. 7,002,342.

(51) Int. Cl.
*G01V 3/00* (2006.01)
(52) U.S. Cl. .................................................... 324/307
(58) Field of Classification Search .......... 324/300–322; 600/410–435
See application file for complete search history.

(56) References Cited

U.S. PATENT DOCUMENTS

| 7,002,342 | B2 * | 2/2006 | Duerk et al. | 324/307 |
| 7,348,776 | B1 * | 3/2008 | Aksoy et al. | 324/307 |
| 7,830,144 | B2 * | 11/2010 | Duerk et al. | 324/307 |

* cited by examiner

*Primary Examiner* — Dixomara Vargas

(57) ABSTRACT

A method and system for improving image quality by correcting errors introduced by rotational motion of an object being imaged is provided. The object is associated with a fiducial mark. The method provides a computer executable methodology for detecting a rotation and selectively reordering, deleting and/or reacquiring projection data.

13 Claims, 16 Drawing Sheets

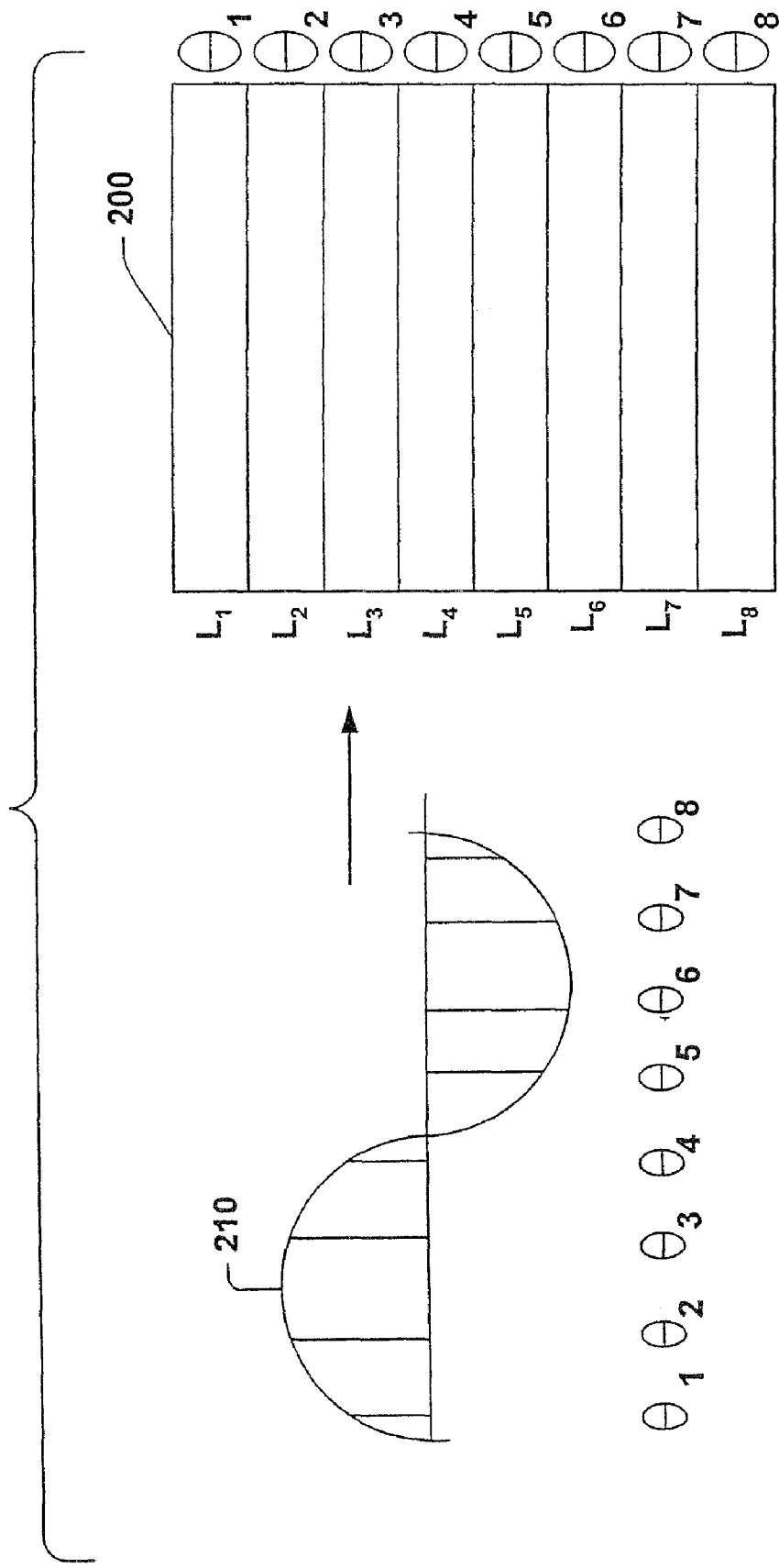

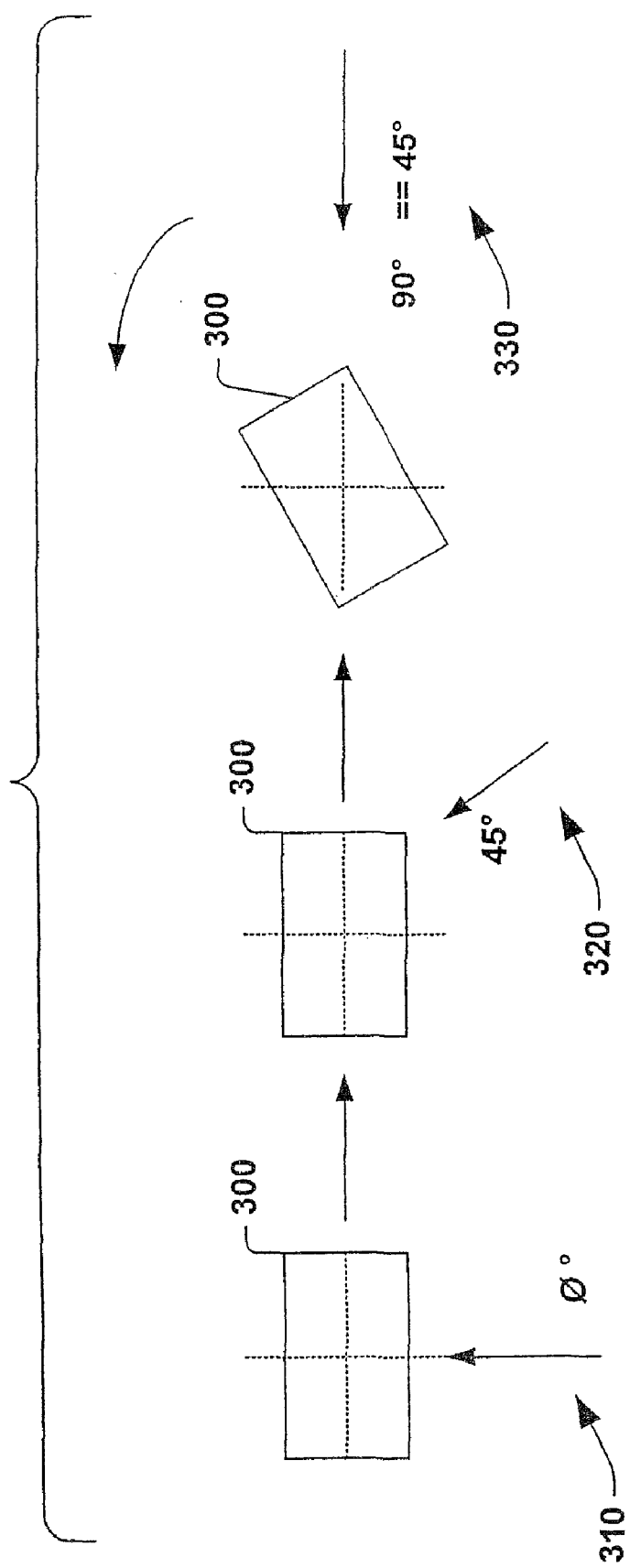

410

400

510

500

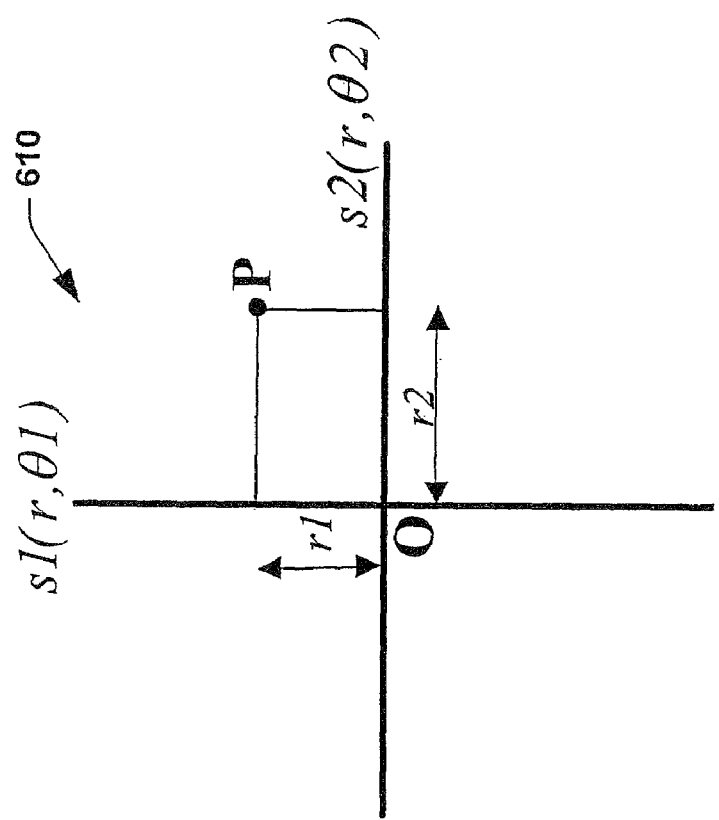
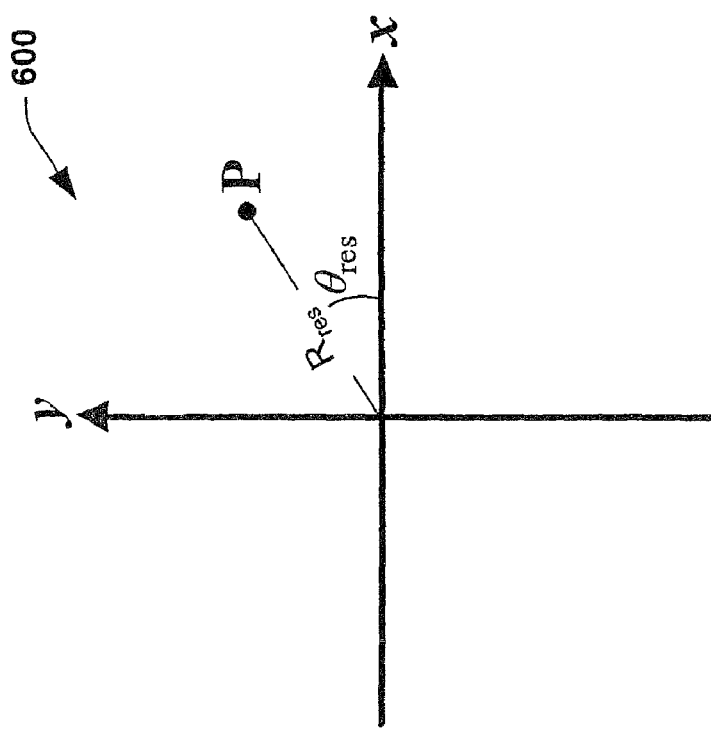
Fig. 6

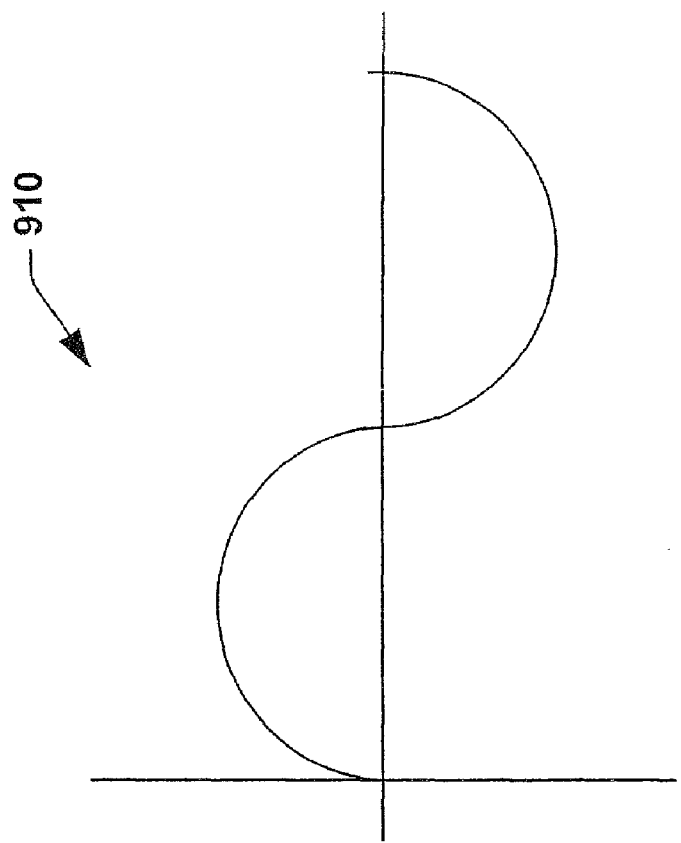
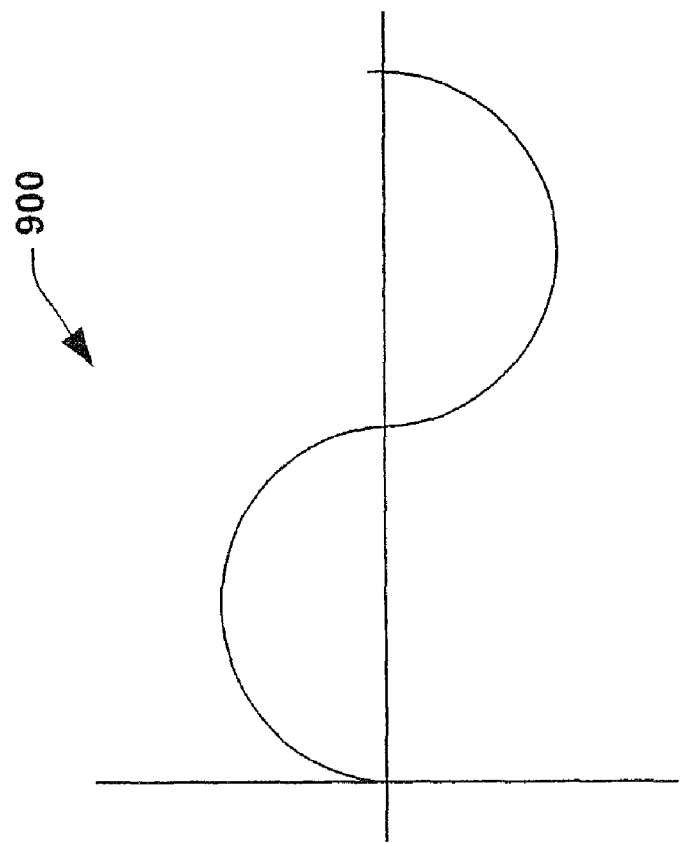
Fig. 9

REDUCING EFFECTS OF ROTATIONAL MOTION

CROSS REFERENCE TO RELATED APPLICATION

This is a Continuation of U.S. Continuation patent application entitled "Reducing Effects of Rotational Motion", Ser. No. 11/224,822; filed Sep. 13, 2005, by inventor Duerk et al.

FEDERAL FUNDING NOTICE

Portions of the claimed subject matter were developed with federal funding.

FIELD OF THE INVENTION

This application relates to the image processing arts and more particularly to improving magnetic resonance imaging (MRI) system images. It will be appreciated that the invention may also have application to other imaging systems (e.g., X-ray, CT, single photon emission computed tomography (SPECT), positron emission tomography (PET),).

BACKGROUND

Magnetic resonance imaging systems acquire diagnostic images without relying on ionizing radiation. Instead, MRI employs strong, static magnetic fields, radio-frequency (RF) pulses of energy, and time varying magnetic field gradient waveforms. Thus, MRI is a non-invasive procedure for producing internal pictures of a subject. Two or three-dimensional diagnostic image data is acquired for respective "slices" of a subject area. These data slices typically provide structural detail having, for example, a resolution of one millimeter or better.

Programmed steps for collecting data that is then used to generate the slices of the diagnostic image are known as a magnetic resonance (MR) image pulse sequence. The MR image pulse sequence includes generating magnetic field gradient waveforms applied along up to three axes, and one or more RF pulses of energy. The set of gradient waveforms and RF pulses are repeated a number of times to collect sufficient data to reconstruct the image slices.

Data is acquired during respective excitations of an MR device. Ideally, there is little or no variation in the nuclear magnetization during the respective excitations. However, movement of the subject caused, for example, by breathing, cardiac pulsation, blood pulsation, and/or voluntary movement, may change the nuclear magnetization from one excitation to the next. Nuclear magnetization changes may degrade the quality of the MR data used to produce the images.

Acquiring an MRI image takes a period of time. The period of time is determined, at least in part, by the number of scans that are taken and the number of data acquisitions in each scan. If the object being imaged moves during the scan then artifacts can be introduced into the image. Very small motions (e.g., 1 mm, 1° of rotation) can introduce artifacts like blurring and ghosting. Some patients may have difficulties lying completely still, which can lead to MRI images of these patients being degraded by a rotational motion. Furthermore, some types of motion (e.g., heartbeat, respiration) require additional technologies for reducing the effects on imagery. Since these technologies may not yield ideal results, they too can lead to the degradation of MRI images due to rotational motion.

SUMMARY

This section presents a simplified summary of methods, systems and computer readable media for improving MRI images that are degraded by rotational motion during MRI. This summary is not an extensive overview and is not intended to identify key or critical elements of the methods, systems, computer readable media and so on or to delineate the scope of these items. This summary provides a conceptual introduction in a simplified form as a prelude to the more detailed description that is presented later.

This application describes a computer implemented method for reducing the effects on image quality of rotational motion that occurs during MRI image acquisition. The method includes receiving and analyzing data about a fiducial mark associated with the object being imaged. A point source location of the fiducial can be computed from this point source data. A predicted sine wave in projection data that will be traced by the point source during the acquisition of radial k-space data can be computed. The method also includes receiving MRI image data of the object. This image data can include, but is not limited to, one or more projections in the radial k-space associated with the object and an observed waveform that can be related to the predicted sine wave. The method also includes comparing the predicted sine wave to the observed waveform and, based on the comparison, selectively processing the image data to reduce the effects of a rotational motion of the object on the image. In one example, the selectively processed image data is then employed to construct a viewable image of the object.

The application also describes a system for improving the quality of an image of an object where the image is degraded by rotational motion of the object during image acquisition. The system includes a data receiver that receives MRI image data from the object being imaged. The image data can include, but is not limited to, object data and fiducial data. The data is stored in one or more data stores, where the object and fiducial data can be stored individually and/or collectively. The system includes a fiducial analyzer that determines a reference sinusoidal fiducial trajectory data and an actual fiducial trajectory data. After these data are computed, the fiducial analyzer may compare the actual trajectory data with the reference sinusoidal fiducial trajectory data to determine whether and/or how to selectively manipulate the object data to improve the quality of the image. The determination is based on whether the comparison indicates that the image was degraded by rotational motion of the object during image acquisition. The system may be integrated into and/or retrofitted into an MRI system.

Certain illustrative example methods, systems, and computer readable media are described herein in connection with the following description and the annexed drawings. These examples are indicative, however, of but a few of the various ways in which the principles of the methods, systems and computer readable media may be employed and thus are intended to be inclusive of equivalents. Other advantages and novel features may become apparent from the following detailed description when considered in conjunction with the drawings.

BRIEF DESCRIPTION OF THE DRAWINGS

FIG. 2 illustrates an example data structure for storing a set of projection data.

FIG. 3 illustrates example relationships between viewing angles and rotational corrections.

FIG. 6 illustrates example measurements employed in correcting for rotational motion.

FIG. 9 illustrates two example waveforms, one collected during an MRI and one predicted from a point source data.

DETAILED DESCRIPTION

Figure 1:
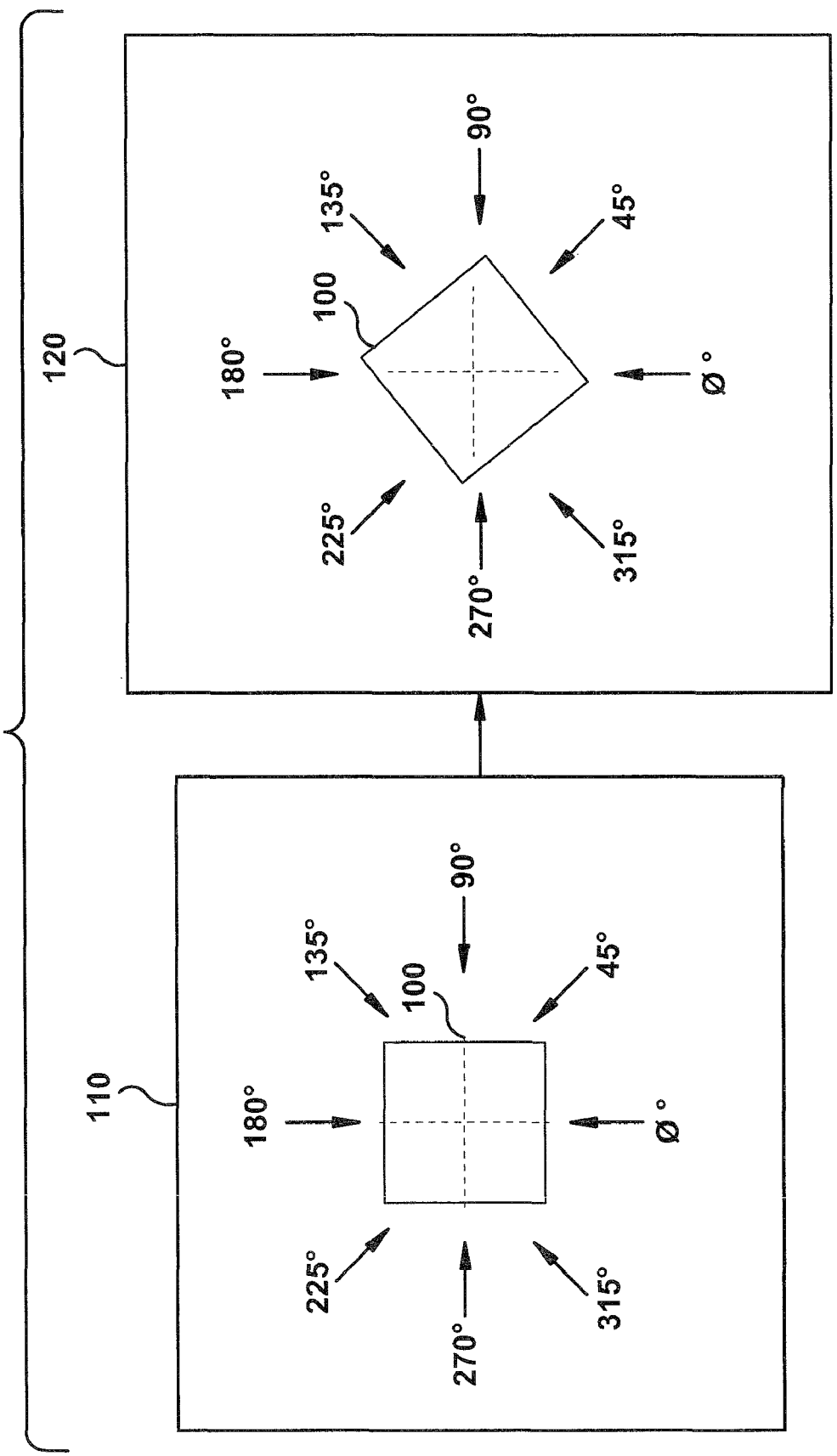
FIG. 1 illustrates example projection angles employed in a radial k-space MRI, and an object before and after rotational motion.

Example methods, systems and computer media are now described with reference to the drawings where like reference numerals are used to refer to like elements throughout. In the following description, for purposes of explanation, numerous specific details are set forth to explain the methods, systems, and computer readable media. It may be evident, however, that the methods, systems, and computer readable media can be practiced without these specific details. In other instances, well-known structures and devices are shown in block diagram form in order to simplify description.

As used in this application, the term "computer component" refers to a computer-related entity, either hardware, firmware, software, a combination thereof, or software in execution. For example, a computer component can be, but is not limited to being, a process running on a processor, a processor, an object, an executable, a thread of execution, a program and a computer. By way of illustration, both an application running on a server and the server can be computer components. One or more computer components can reside within a process and/or thread of execution and a computer component can be localized on one computer and/or distributed between two or more computers.

"Software", as used herein, includes but is not limited to, one or more computer readable and/or executable instructions that cause a computer or other electronic device to perform functions, actions and/or behave in a desired manner. The instructions may be embodied in various forms (e.g., routines, algorithms, modules, methods, threads, programs). Software may also be implemented in a variety of executable and/or loadable forms including, but not limited to, a stand-alone program, a function call (local and/or remote), a servelet, an applet, instructions stored in a memory, part of an operating system or browser, and so on. It is to be appreciated that the computer readable and/or executable instructions can be located in one computer component and/or distributed between two or more communicating, co-operating, and/or parallel processing computer components and thus can be loaded and/or executed in serial, parallel, massively parallel, and other manners.

To facilitate understanding correcting for the rotational motion of an object during radial k-space image acquisition, imagine standing directly in front of a person. You are looking directly at the person (e.g., a viewing angle of 0°) and you see their face. For some reason, you want to walk around the person and take 360 photographs, one photograph for each degree of the compass. As you work your way around the person you eventually get exactly half way around (e.g., 180°). Imagine at this point in time, that the person rotates 180° so that you are once again directly face to face. You now move 1° further around your circle and take the next image. While the image is still good data, instead of it being an image taken from 181° (e.g., behind the person you are photographing), it is a repeat of the image from 1°. Thus, when you develop your pictures, you will have two images taken from one degree relative to the face of the person and no images taken 181° relative to the person.

Imagine further that as you reached exactly half way around the person you are photographing, that instead of rotating exactly 180° to face you, they rotate 90° counter to the direction you are walking around them. As you completed your circle around the person, the remainder of the images you acquire would be 90° out of phase. In addition to having 90 duplicate photographs, there would be 90° for which you had no photographs of the person. Thus, example systems and methods described herein use fiducials placed on and/or in the object being imaged to facilitate detecting this type of rotational motion and correcting errors associated with the rotational motion. While this analogy describes photography, it is to be appreciated that this application relates to MRI, PET, CT, optical imaging and so on, in which projection data are used to reconstruct cross-sectional images.

Referring initially to FIG. 1, two views of an object 100 are illustrated. In the first view 110, object 100 is at an initial orientation where various projection angles employed in radial k-space MRI are illustrated relative to the object 100. For example, view angles starting at 0° and progressing by 45° to 315° are illustrated. While eight projection angles are illustrated, it is to be appreciated that a greater and/or lesser number of projection angles can be employed in radial k-space MRI. In one example, 360 projection angles can be employed starting at 0° and increasing in one degree increments.

In view 120, object 100 has undergone rotational motion. Thus, the radial k-space data collected from various projection angles after the rotation may not accurately reflect the projection angle desired. Thus, rotational motion of object 100 during MRI image acquisition can negatively affect image quality. In one example, rotational motion of object 100 can be detected based, at least in part, on a fiducial marker placed on and/or in a subject being imaged.

Turning now to FIG. 2, an example data structure 200 that stores a set of projection data 210 is illustrated. Data structure 200 can be, for example, an array addressed to facilitate retrieving projection data by projection angle. For example, a first signal acquired at projection angle $\theta_1$ can be stored in data structure 200 at location $L_1$. Similarly, a second signal acquired at projection angle $\theta_2$ can be stored in data structure

200 at location $L_2$. Although the signals can be acquired sequentially (e.g., $\theta_1, \theta_2, \ldots \theta_8$), it is to be appreciated that the data can be acquired in other orders that are neither linear nor sequential. However, storing the data from the various projection angles in data structure 200 in predetermined locations associated with the programmed projection angles facilitates selectively processing (e.g., re-ordering) the acquired data. While an array is illustrated in FIG. 2, it is to be appreciated that other data structures and/or data stores including, but not limited to, trees, tables, lists, files, and so on, may be employed in accordance with various aspects of this application. The rotational motion described in FIG. 1 can lead to projection data being stored in locations that do not correspond to actual locations, which can negatively affect image quality.

FIG. 3 illustrates example relationships between viewing angles and rotational movements that facilitate correcting for rotational motion during MRI image acquisition. An object 300 may first be imaged from a viewing angle 0° as illustrated at 310. Data from this view angle can be stored in an addressable data structure at a location programmatically associated with the view angle. Subsequently, object 300 maybe viewed from an angle of 45° as illustrated at 320. Data from this subsequent view angle can also be stored in an addressable data structure at a location programmatically associated with the subsequent view angle. Thereafter, object 300 may rotate counterclockwise 45°. If object 300 were then imaged from an angle of 90° as illustrated at 330, this would be equivalent to re-imaging the object 300 from an angle of 45° as illustrated at 320. Data from this view angle may conventionally be incorrectly stored at a location programmatically associated with 90° instead of 45°. Thus, there would be two sets of data for the projection angle of 45° (one stored correctly, one stored incorrectly) and no projection data for the projection angle of 90°. In conventional systems that do not account for the rotational motion of the object 300, the data presumably acquired at 90° would be incorrectly stored for the 90° projection angle. Example systems and methods described herein facilitate detecting rotational motion of object 300 and determining where, if anywhere, the unanticipated projection angle data should be stored and how it should be processed. In one example, fiducial markers on and/or in object 300 may facilitate detecting the rotational motion.

Figure 4B:
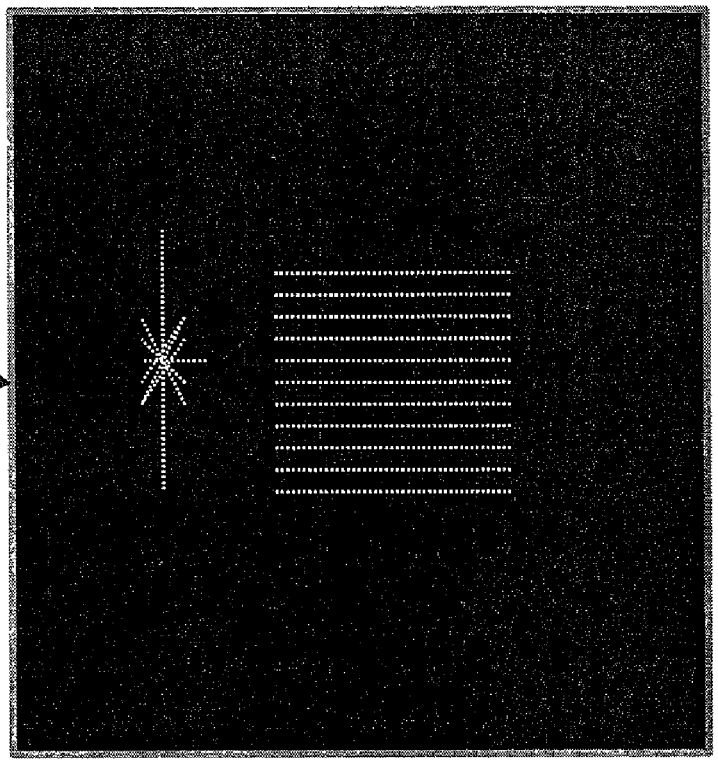
FIGS. 4a and 4b illustrate example MRI images before and after correction for rotational motion.
Figure 4A:
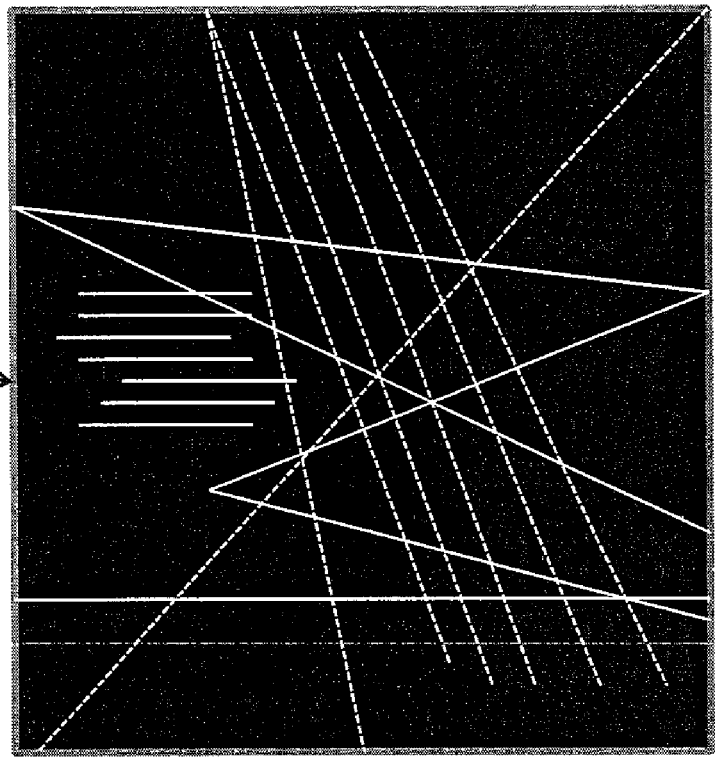

Turning now to FIGS. 4a and 4b, two images illustrate example MRI images before (FIG. 4a) and after (FIG. 4b) correction for rotational motion. Image 400 is an MRI image before correction, where the image is degraded due to rotational motion of the object during image acquisition. Image 410 is an MRI image of the same item after detecting errors due to rotational motion and correcting for those errors. A bright spot in the top center of image 410 represents an image marker (e.g., fiducial) placed on, in, and/or near but associated with the object. This "fiducial" marker will be described in greater detail below.

Figure 5B:
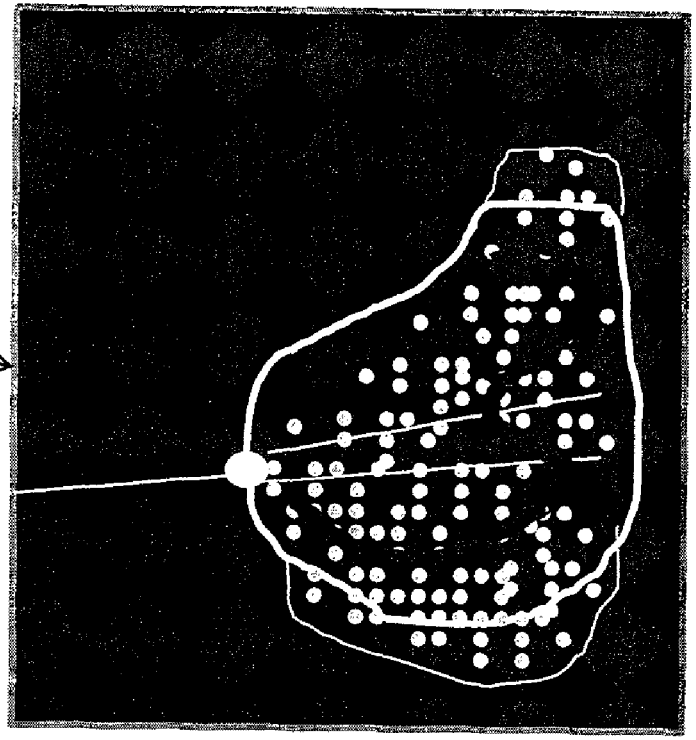
FIGS. 5a and 5b illustrates example MRI images before and after correction for rotational motion.
Figure 5A:
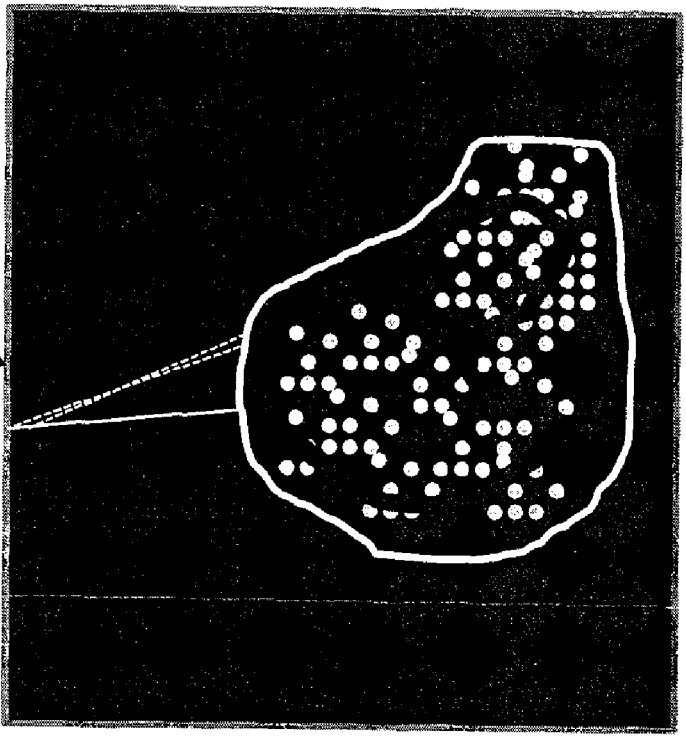

FIGS. 5a and 5b similarly illustrate before and after representations of MRI images. For example, image 500 is an uncorrected image of a knee that rotated during the acquisition of the MRI image. Image 510 is an image of the knee after the rotational motion has been detected and corrective steps have been taken. Again, notice the bright spot in the top center of image 510. The bright spots in FIGS. 4b and 5b are associated with a fiducial mark associated with the object to be imaged. In one example, a high signal fiducial mark (e.g., gadolinium filled tuned fiducial marker) facilitates receiving fiducial data from an object being imaged. It is to be appreciated that while the fiducial mark may be placed on the object to be imaged, the fiducial may also be placed near the object to be imaged and/or can be associated with the object to be imaged so that it if the object rotates the fiducial will also rotate. It is to be further appreciated that more than one fiducial may be associated with the object to be imaged, which would produce one or more reference waveforms that could be analyzed by the systems and methods described herein.

Figure 7B:
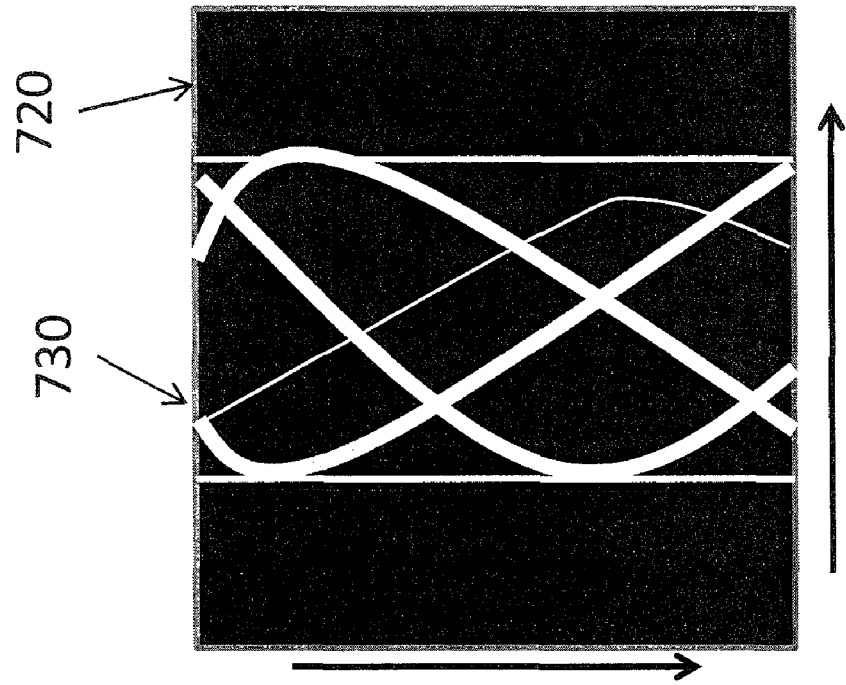
FIGS. 7a and 7b illustrate an example point source, image space, and sinogram space.
Figure 7A:
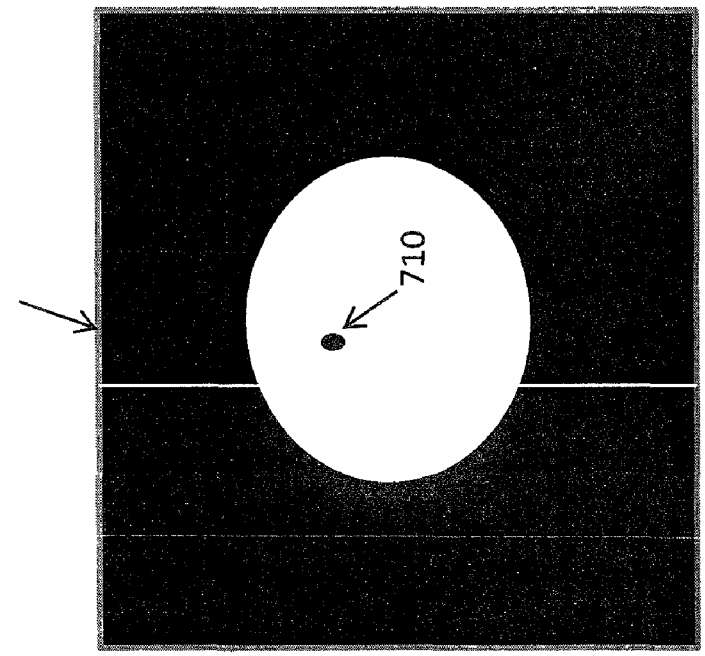

FIGS. 6, 7a, and 7b show a relationship between an image space and a sinogram space. A sinogram is a two-dimensional map representing the amplitude of a signal as a function of its position along a projection direction along one axis, with the other axis representing the projection angle. Note that a point source in the image space transforms into a unique sine wave in the sinogram space. This sine wave can also be recreated from, at minimum, two projections. This is a direct result of Shannon's sampling theorem. For example, take two projections of a point source P, $s1(r, \theta_1)$ and $s2(r, \theta_2)$, at angles $\theta_1=0°$ and $\theta_2=90°$, respectively. Illustration 600 shows the imaging coordinate system and the point source P. Illustration 610 shows the two projections about the center of rotation O. r1 and r2 represent the projected distance of P on s1 and s2, respectively, from the center of rotation of the projections, O. If this point source rotates with the imaged object during the acquisition of the radial data, the sine wave corresponding to the point source will be disrupted. The disrupted waveform can, theoretically, be extracted from the sinogram data using an edge detection algorithm and/or other detection algorithm, methods, apparatus and processes.

FIG. 6 illustrates fiducial mark measurements that facilitate detecting and/or correcting for rotational motion of an object being imaged. Illustrations 600 and 610 show a point P that is associated with the fiducial mark. A first projection taken at a viewing angle of $\theta_1$ results in a projection data $S_1$ from which a projection distance $r_1$ can be computed. A second projection taken at a viewing angle of $\theta_2$ yields a second projection data $S_2$ from which a second projected distance $r_2$ can be acquired. This first projection data and second projection data can be referred to as a point source data. In one example, the viewing angles $\theta_1$ and $\theta_2$ are orthogonal to each other, which facilitates subsequent rotational motion detection and correction. While two projection data are illustrated at 610, it is to be appreciated that a greater number of projections can be employed to produce the point source data. Additionally, it is to be appreciated that the projection data that forms the point source data can be acquired at times including, but not limited to, before imaging the object, while acquiring the MRI image, and after acquiring the MRI image. In one example, the first projection data $S_1$ and the second projection data $S_2$ are repetitively acquired until it is mathematically verifiable that no rotational motion occurred between acquiring the two data. This facilitates detecting and correcting for rotational motion of an imaged object.

Once point source data has been acquired, a point source location can be computed from the point source data. For example, in illustration 600, a $\theta_{res}$ and an $R_{res}$ can be computed from $S_1$ and $S_2$ to simplify subsequent mathematical calculations for detecting and correcting for rotational motion. In one example, $R_{res}$ is determined according to $R_{res}=$ the square root of $(r_1^2+r_2^2)$. Similarly, in one example, $\theta_{res}$ is determined according to $\theta_r=\tan^{-1}(r_2/r_1)$. Once $\theta_{res}$ and $\theta_{res}$ have been computed, a predicted sine wave that will be traced by the fiducial mark can be computed. In one example, the predicted sine wave is calculated according to $\sin_{res}=(R_{res})\cos(|\theta_{res}-\theta|)$, where $\theta$ can vary throughout a range of viewing angles.

Thus, referring to the calculations associated with FIG. 6, two projections are taken at viewing angles $\theta_1$ and $\theta_2$, preferably where $\theta_1$ and $\theta_2$ are orthogonal. Preferably, the projections are taken at times between which it can be determined that no rotational motion occurred. Given the two projection data, the values $R_{res}$ and $\theta_{res}$ can be computed. Once $R_{res}$ and $\theta_{res}$ are computed, then a predicted reference waveform that will be produced from the signal generated by the fiducial marker can be computed.

Turning now to FIGS. 7a and 7b, an example point source and the sinogram resulting from a radial k-space data acquisition of an image associated with the point source is presented. In addition to the point source data, data associated with the object with which the point source is associated is also stored. If the system computes how far from an expected location the point source has rotated, then a computation can be made to determine how far to shift the data associated with both the point source and the object to correct for the rotational motion. Thus, a method employing an object associated with a fiducial can include associating the point source 710 with the object to be imaged, computing the point source location, predicting a sine wave 730 that will be produced during radial k-space acquisition of the object data, acquiring a unique actual waveform from the radial projections, comparing the predicted sine wave 730 to the actual unique waveform that is collected during MRI and correcting and/or reacquiring data based on the comparison of the predicted sine wave 730 to the actual waveform.

Figure 8:
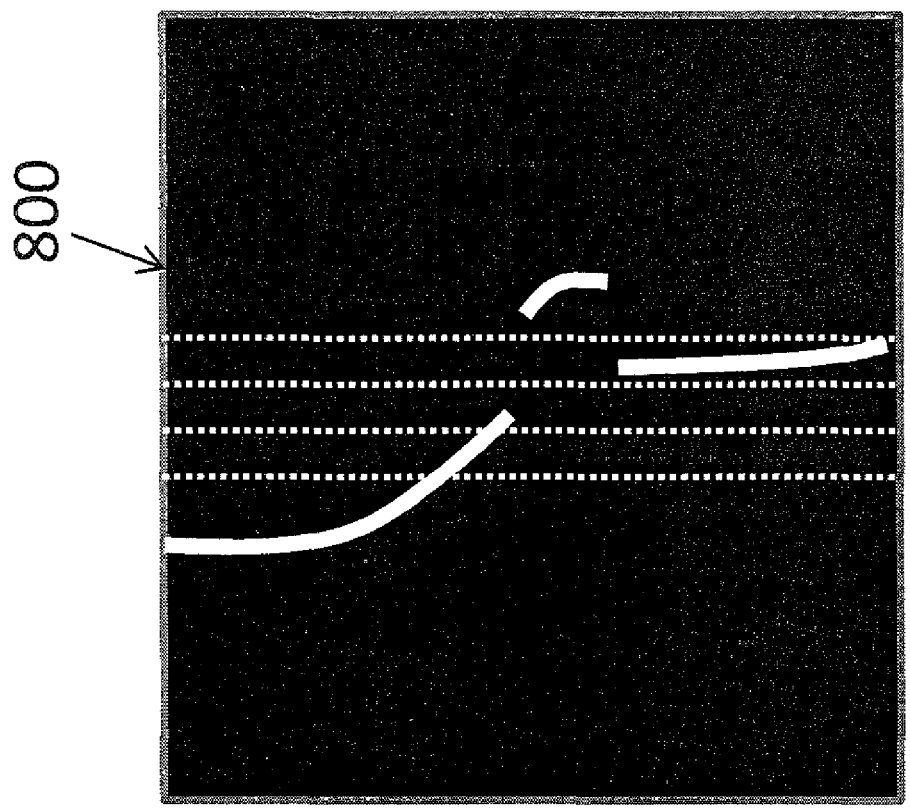
FIG. 8 illustrates an example sinogram exhibiting the results of rotational motion on a reference waveform.

FIG. 8 illustrates an example sinogram exhibiting a result of rotational motion on a reference waveform 800. The reference waveform 800 (brightest line) illustrates a step discontinuity characteristic of a rotational motion of the fiducial marker associated with the object to be imaged. An edge detection algorithm (or other detection method/apparatus) can be used to detect the step discontinuity. By detecting the discontinuity in the reference waveform 800, both the point at which rotational motion occurred, the point at which the object rotated back (if any), and the amount of rotational motion can be computed. While a step discontinuity is illustrated in FIG. 8, it is to be appreciated that other deformations and/or irregularities in an acquired waveform may also be detected.

FIG. 9 illustrates two waveforms. The sine wave 900 is an example of a predicted sine wave while the waveform 910 is an example of an actual waveform acquired during radial k-space MRI. The systems and methods described herein predict the sine wave 900, acquire the waveform 910, and compare the two waveforms to determine whether the data points are within a predetermined, configurable tolerance. If the waveforms are within the tolerances, then the systems and/or methods can proceed to subsequent steps like reconstructing an image from the acquired MRI data. If, however, the comparison produces data outside the tolerances, then additional processing can be selectively undertaken to correct for rotational motion during image acquisition. The additional processing is described in greater detail below.

Figure 10:
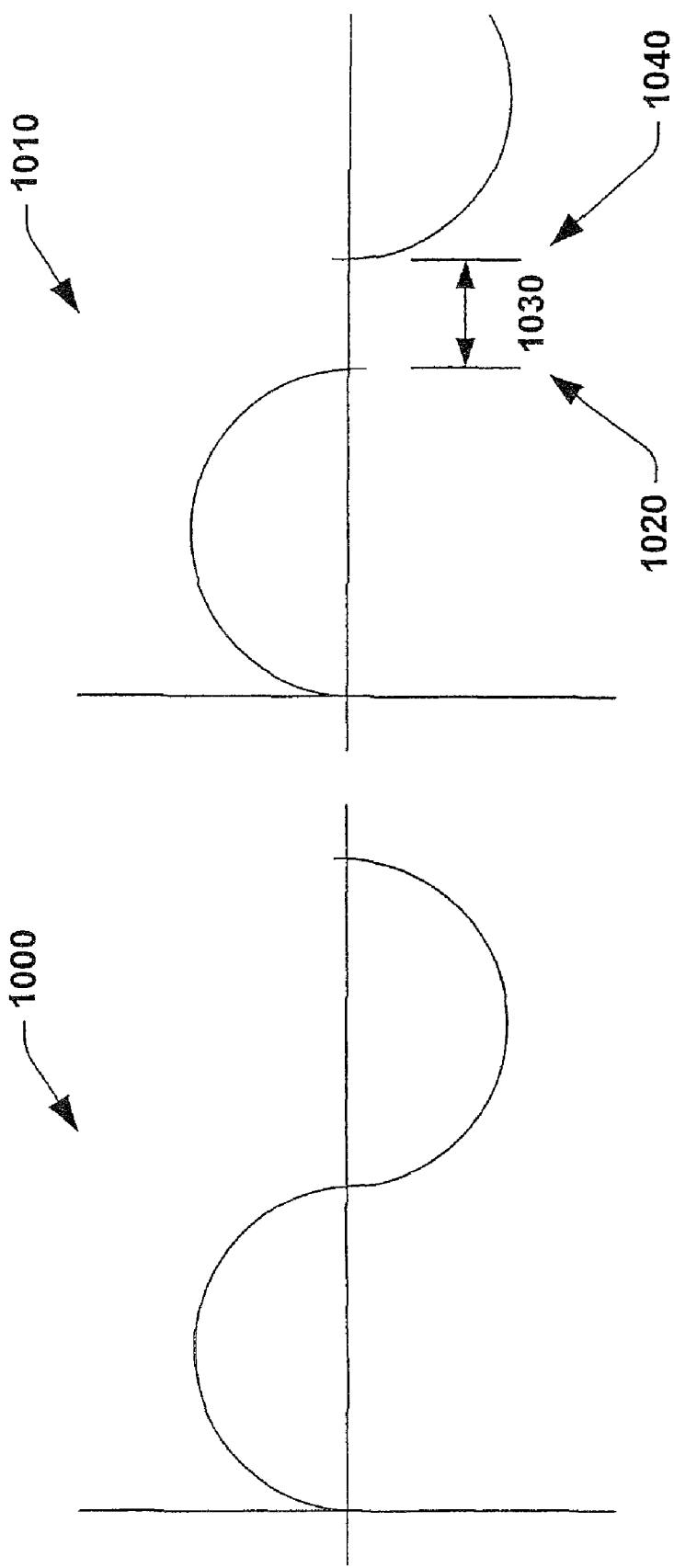
FIG. 10 illustrates two example waveforms, one predicted from a point source data and one collected during an MRI, where the collected waveform exhibits the results of rotational motion during image acquisition.

Turning to FIG. 10, an example waveform 1010 collected during an MRI where the wave exhibits the results of rotational motion is illustrated alongside a predicted sine wave 1000. The predicted sine wave 1000 was computed from point source data acquired from a fiducial associated with the object to be imaged. The actual wave 1010 was then collected from the MRI data. As seen, the actual wave 1010 is distorted starting at an identifiable point 1020 at which a rotational motion occurred. Furthermore, the disrupted wave 1010 facilitates identifying a point 1040 at which the rotational motion ceased. The interval 1030 facilitates identifying, for example, the magnitude and/or direction of the rotation. As described earlier, a rotational motion can lead to gaps in the projection data and/or duplicate projection data. Therefore, based on the location 1020, the interval 1030, and the location 1040, MRI image data can be selectively processed to correct for the rotational motion. The selective processing can include, but is not limited to, re-ordering the data, removing one or more projection data from the set of projection data acquired during MRI, and generating a signal to indicate that additional projection data should be acquired. When a signal is generated to indicate that additional projection data should be acquired, systems and methods described herein may then receive the additional projection data and update the data that produced wave 1010 to facilitate recomparing the predicted sine wave with an updated waveform. In one example, the steps of generating a signal to indicate that additional projection data should be acquired, receiving the additional projection data, updating the observed waveform, and comparing the predicted sine wave with the updated waveform can occur repeatedly. For example, they may repeat until a comparison of the predicted dine wave and the updated observed waveform is within a predetermined configurable tolerance and/or until a predetermined, configurable number of attempts have been made.

Since the comparison of the predicted sine wave with the acquired waveform can be performed by distributed systems and/or methods operating substantially in parallel with an MRI system, which may be distinct from the systems for acquiring the MRI data, it is to be appreciated that the systems and methods described herein for detecting rotational motion of an object should not increase MRI scan times. While the computations do not increase the scan time, one example method facilitates improving a signal to noise ratio in the observed image data by at least 50%. By recognizing the location, direction, and magnitude of a rotational motion, "errors" can be removed from acquired data which leads to the improvement in the signal to noise ratio. In another example, systems and methods described herein facilitate improving the signal to noise ratio in the selectively processed observed image data to within 33% of what the signal to noise ratio would be in a corresponding image data that was not disrupted by rotational motion. The ability to undertake processing like removing duplicate data, averaging duplicate data, acquiring data that was initially missed, re-ordering data that has been stored in an incorrect location, and the like, facilitates producing these improvements in general image quality. Improvements can be noted in measurements including, but not limited to, signal to noise ratios, resolution, level of artifacts, and so on.

As described above, the observed image data received from an MRI scan of an object includes the projection data of a radial k-space associated with the object and an observed waveform associated with the fiducial associated with the object that is scanned. However, the data associated with the fiducial may leave an artifact in the observed image data. Therefore, in one example method, additional processing is performed to remove the waveform data from the image data associated with the fiducial.

While the systems and methods described herein facilitate identifying and correcting for rotational motion during image acquisition, it is to be appreciated that once detection and correction have been undertaken, example systems and methods may subsequently construct an image of the object based on observed image data that has been selectively processed to correct for rotational motion. It is to be further appreciated that the processing performed to correct for rotational motion during image acquisition may be employed in systems and methods that also undertake processing designed to reduce the effects of translational motion of the object to be imaged. In one example, the translational motion correction is undertaken before the correction for rotational motion.

Figure 11:
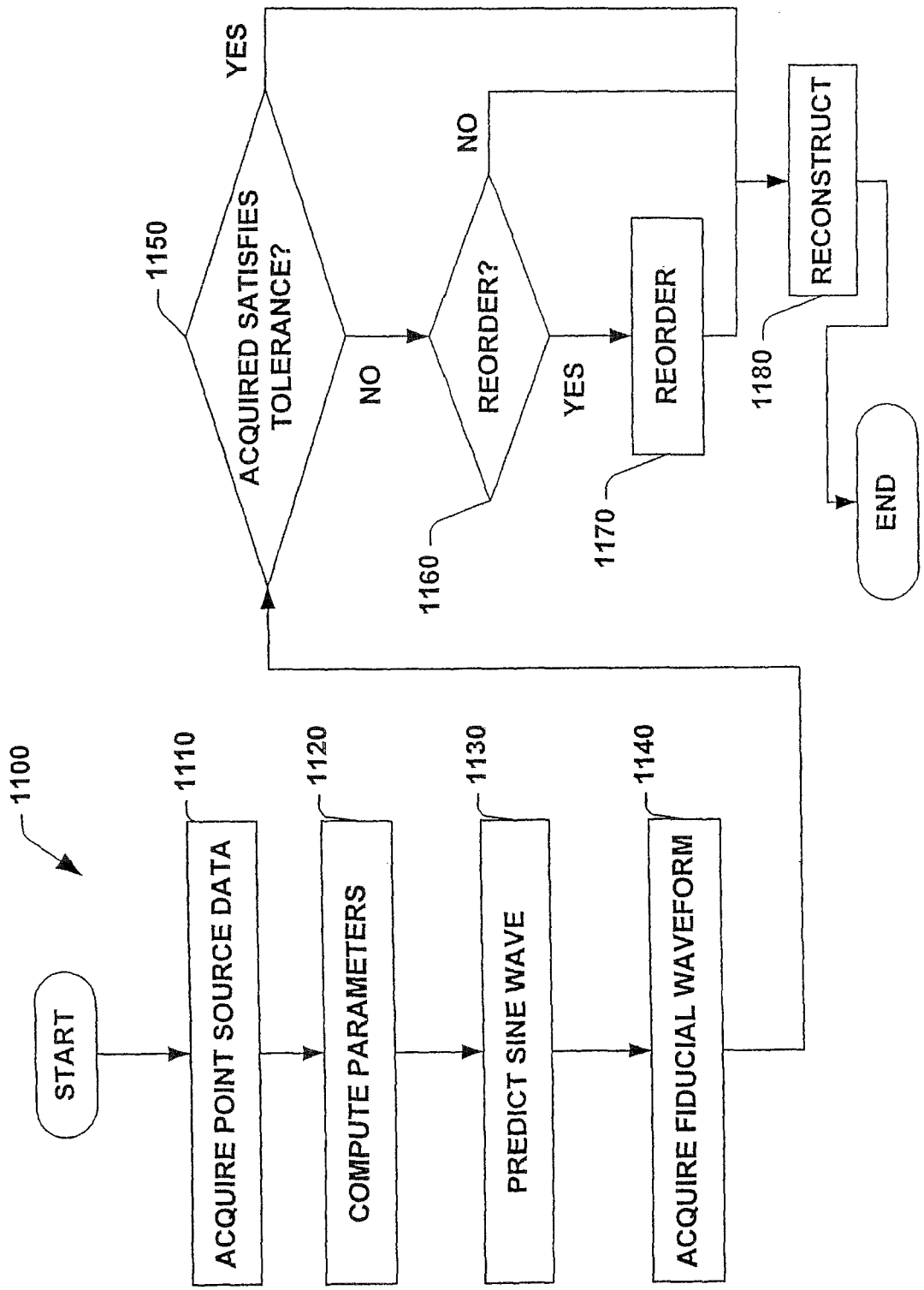
FIG. 11 illustrates an example method for reducing the effects on image quality of rotational motion of an object during image acquisition.
Figure 12:
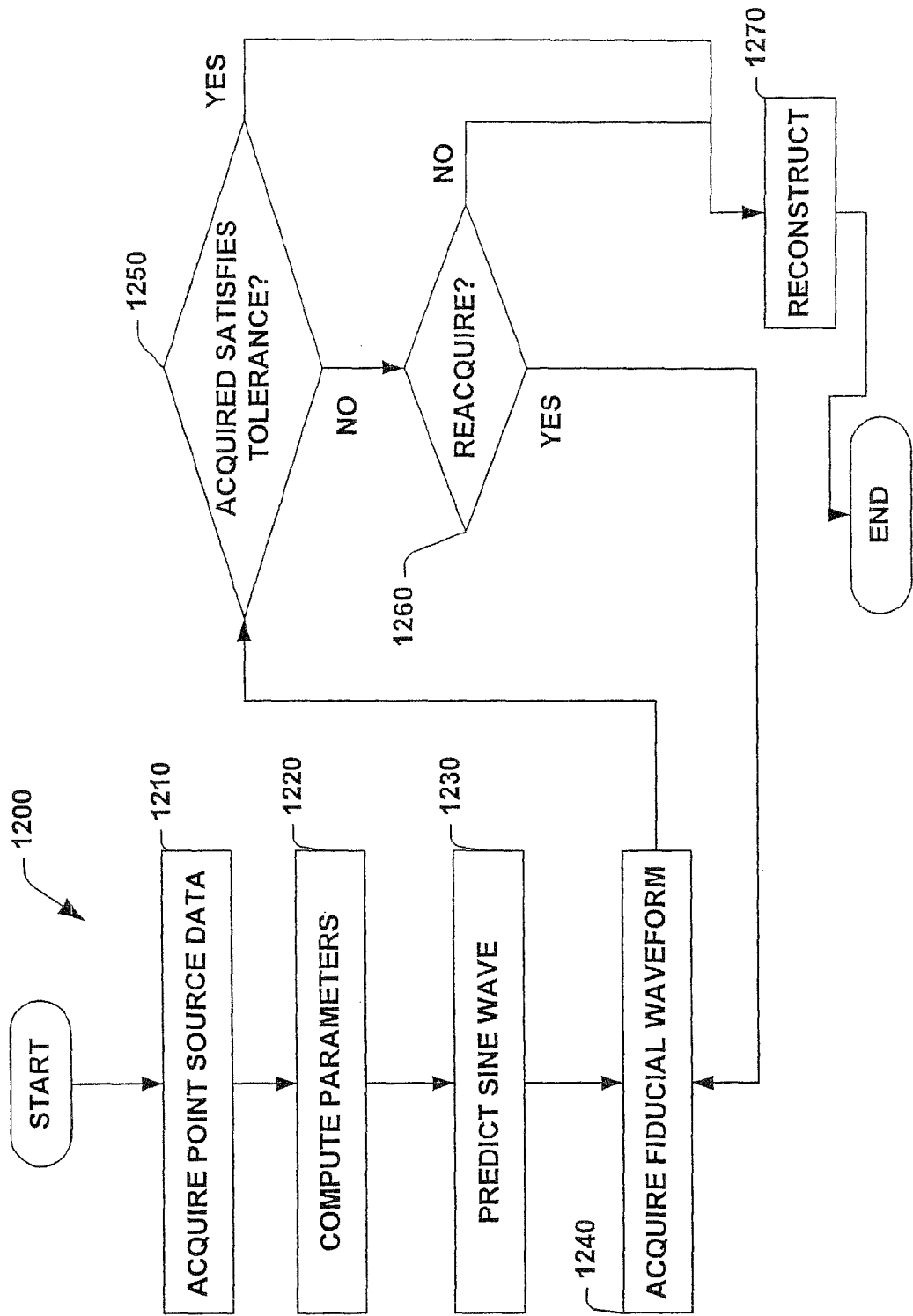
FIG. 12 illustrates an example method for reducing the effects on image quality of rotational motion of an object during image acquisition.

In view of the exemplary systems shown and described herein, example computer implemented methods will be better appreciated with reference to the flow diagrams of FIGS. 11 and 12. While for purposes of simplicity of explanation, the illustrated methods are shown and described as a series of blocks, it is to be appreciated that the methods are not limited by the order of the blocks, as some blocks can occur in different orders and/or concurrently with other blocks from that shown and described. Moreover, less than all the illustrated blocks may be required to implement an example method. Furthermore, additional and/or alternative methods may employ additional, not illustrated blocks. In one example, methods are implemented as computer executable instructions and/or operations stored on a computer-readable media. It is to be appreciated that the methods can be implemented in software as that term is defined herein.

In the flow diagrams, rectangular blocks denote "processing blocks" that may be implemented, for example, in software. Similarly, the diamond shaped blocks denote "decision blocks" or "flow control blocks" that may also be implemented, for example, in software. Alternatively, and/or additionally, the processing and decision blocks can be implemented in functionally equivalent circuits like a digital signal processor (DSP), an application specific integrated circuit (ASIC), and the like.

A flow diagram does not depict syntax for any particular programming language, method, or style (e.g., procedural, object-oriented). Rather, a flow diagram illustrates functional information one skilled in the art may employ to program software, design circuits, and so on. It is to be appreciated that in some examples, program elements like temporary variables, routine loops, and so on are not shown.

Referring now to FIG. 11, a flow chart illustrates an example method 1100 for reducing the effects on image quality of rotational motion of an object during MRI image acquisition. At 1110, point source data is acquired. This point source data can include measurements like the angles of projection employed in characterizing the point source, and resulting distances associated with characterizing the point source.

At 1120, point source parameters can be computed. For example, parameters $R_{res}$ and $\theta_{res}$ can be computed from the point source data acquired at 1110. At 1130, based, at least in part, on the parameters computed at 1120 and/or the point source data acquired at 1110, a unique sine wave that will be produced by the point source during radial k-space MRI can be predicted. At 1140, waveform data associated with the point source is acquired from the object being imaged. While blocks 1130 and 1140 illustrate predicting the sine wave and then acquiring the waveform data, it is to be appreciated that such predictions and acquisitions can occur substantially in parallel.

At 1150, a determination is made concerning whether the acquired waveform data satisfies pre-determined, configurable tolerances when compared to the predicted sine wave data. For example, the sum of the absolute values of the differences of predicted points on a sine wave with acquired points on a waveform can be computed. If the determination at 1150 is yes, then processing proceeds to 1180 where the object image is reconstructed from the acquired data. However, if the determination at 1150 is no, then at 1160 a determination is made concerning whether to re-order one or more projection data points. If the determination at 1160 is yes, then the projection data will be re-ordered at 1170. For example, data placed in a first location corresponding to a first, incorrect view angle may be moved to a second, correct view angle location. Additionally, and/or alternatively, the data may be averaged with data already stored in the correct view angle location, may replace the data already stored in the correct view angle location or may be employed to correct data stored in the correct view angle location. The determination at 1160 may be no if, for example, the differences between the predicted sine wave data and the acquired waveform data exceed a predetermined, configurable threshold indicating that re-ordering would not produce a desired reduction in signal to noise ratio. In this case, method 1100 may be extended to include restarting the image acquisition sequence.

FIG. 12 illustrates an example method 1200 for reducing the effects on image quality of rotational motion of an object during MRI image acquisitions. While the methods 1100 and 1200 are discussed in connection with MRI, it is to be appreciated that in different examples the systems and methods described herein can be employed where an object is imaged through techniques including, but not limited to, magnetic resonance imaging, x-ray imaging, CT, SPECT, optical imaging techniques and positron emission tomography. The optical imaging techniques can include, but are not limited to, techniques involving bio-luminescence and fluorescence.

At 1210, point source data is acquired and at 1220 point source parameters are computed from the point source data. Thus, the location of a fiducial associated with an object to be imaged can be computed which facilitates, at 1230, predicting a unique sine wave that will be produced during the imaging of the object. At 1240, observed waveform data from the fiducial mark is acquired. Thus, at 1250, a determination is made concerning whether the acquired waveform data is within predetermined, configurable tolerances of the sine wave predicted at 1230. If the determination at 1250 is yes, then processing continues at 1270 where the image of the object is reconstructed. If, however, the determination at 1250 is no, then at 1260, a determination is made concerning whether to reacquire one or more points of waveform data by, for example, repositioning imaging means that selectively acquire one or more projection data from one or more viewing angles. If the determination at 1260 is no, then at 1270, an image of the object is reconstructed. But if the determination at 1260 is yes, then processing returns to 1240. In one example method, the determination at 1260 may depend, at least in part, on a predetermined, configurable number of attempts having been made to reacquire data and/or whether the method 1200 should be restarted.

Figure 13:
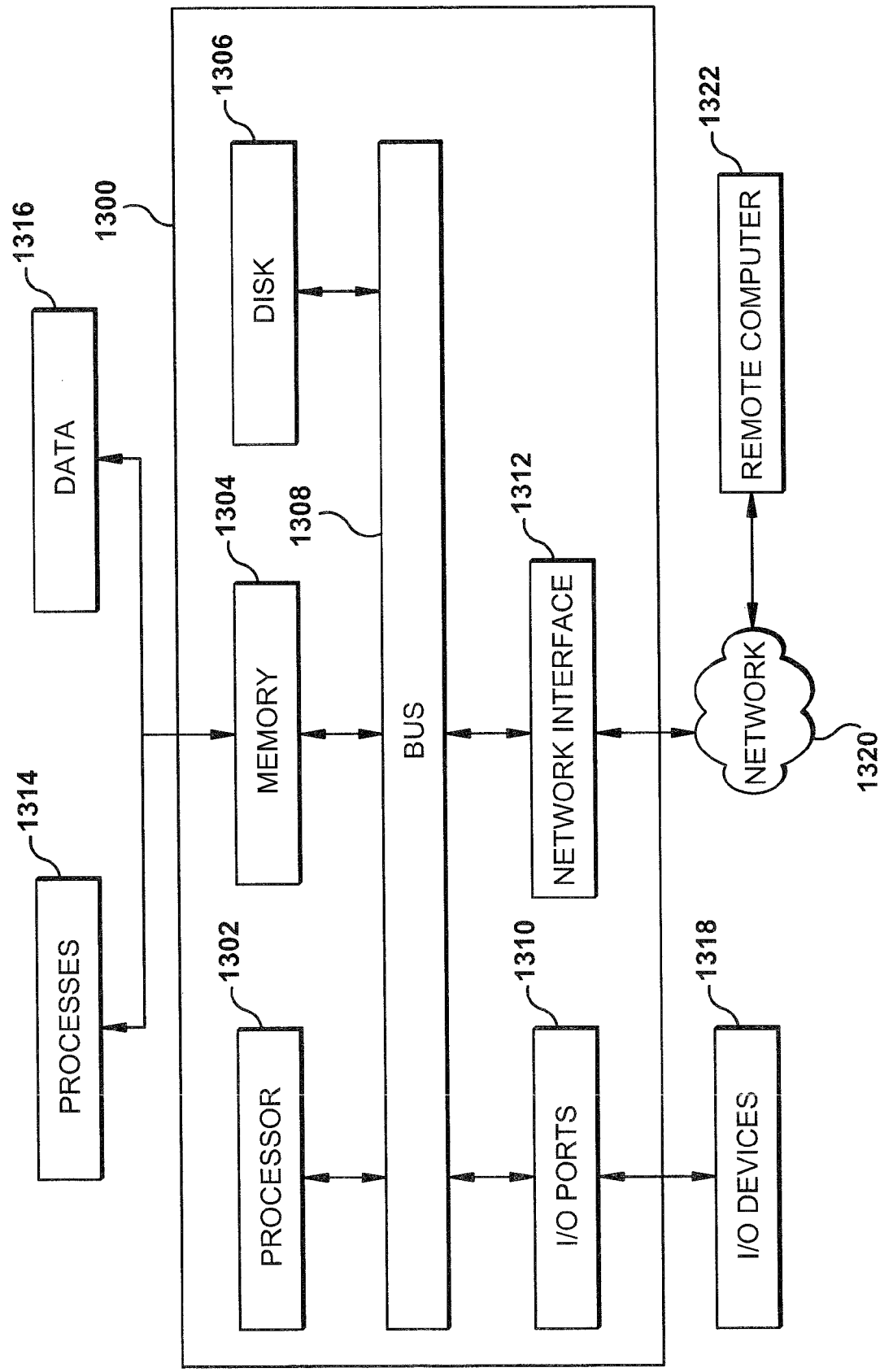
FIG. 13 is a schematic block diagram of an example computing environment with which the systems, methods and computer readable media described herein may interact.

FIG. 13 illustrates a computer 1300 that includes a processor 1302, a memory 1304, a disk 1306, input/output ports 1310, and a network interface 1312 operably connected by a bus 1308. Executable components of the systems described herein may be located on a computer like computer 1300. Similarly, computer executable methods described herein may be performed on a computer like computer 1300. It is to be appreciated that other computers may also be employed with the systems and methods described herein. Furthermore, it is to be appreciated that the computer 1300 can be located locally to an MRI system, remotely to an MRI system and/or can be embedded in an MRI system.

Processor 1302 can be a variety of various processors including dual microprocessor and other multi-processor architectures. Memory 1304 can include volatile memory and/or non-volatile memory. The non-volatile memory can include, but is not limited to, read only memory (ROM), programmable read only memory (PROM), electrically programmable read only memory (EPROM), electrically erasable programmable read only memory (EEPROM), and the like. Volatile memory can include, for example, random access memory (RAM), synchronous RAM (SRAM), dynamic RAM (DRAM), synchronous DRAM (SDRAM), double data rate SDRAM (DDR SDRAM), and direct RAM bus RAM (DRRAM). Disk 1306 can include, but is not limited to, devices including a magnetic disk drive, a floppy disk drive, a tape drive, a Zip drive, a flash memory card, and/or a memory stick. Furthermore, disk 1306 can include optical drives including a compact disk ROM (CD-ROM), a CD recordable drive (CD-R drive), a CD rewriteable drive (CD-RW drive) and/or a digital versatile ROM drive (DVD ROM). The memory 1304 can store processes 1314 and/or data 1316, for example. Disk 1306 and/or memory 1304 can store an operating system that controls and allocates resources of computer 1300.

Bus 1308 can be a single internal bus interconnect architecture and/or other bus architectures. Bus 1308 can be of a variety of types including, but not limited to, a memory bus or memory controller, a peripheral bus or external bus, and/or a local bus. The local bus can be of varieties including, but not limited to, an industrial standard architecture (ISA) bus, a microchannel architecture (MSA) bus, an extended ISA (EISA) bus, a peripheral component interconnect (PCI) bus, a universal serial bus (USB), and a small computer systems interface (SCSI) bus.

Computer 1300 interacts with input/output devices 1318 via input/output ports 1310. Input/output devices 1318 can include, but are not limited to, a keyboard, a microphone, a pointing and selection device, cameras, video cards, displays, and so on. Input/output ports 1310 can include but are not limited to, serial ports, parallel ports, and USB ports.

Computer 1300 can operate in a network environment and thus is connected to a network 1320 by a network interface 1312. Through network 1320, computer 1300 may be logically connected to a remote computer 1322. Network 1320 includes, but is not limited to, local area networks (LAN), wide area networks (WAN), and other networks. Network interface 1312 can connect to local area network technologies including, but not limited to, fiber distributed data interface (FDDI), copper distributed data interface (CDDI), ethernet/IEEE 802.3, token ring/IEEE 802.5, and so on. Similarly, network interface 1312 can connect to wide area network technologies including, but not limited to, point to point links, and circuit switching networks (e.g., integrated services digital networks (ISDN)), packet switching networks, and digital subscriber lines (DSL).

Figure 14:
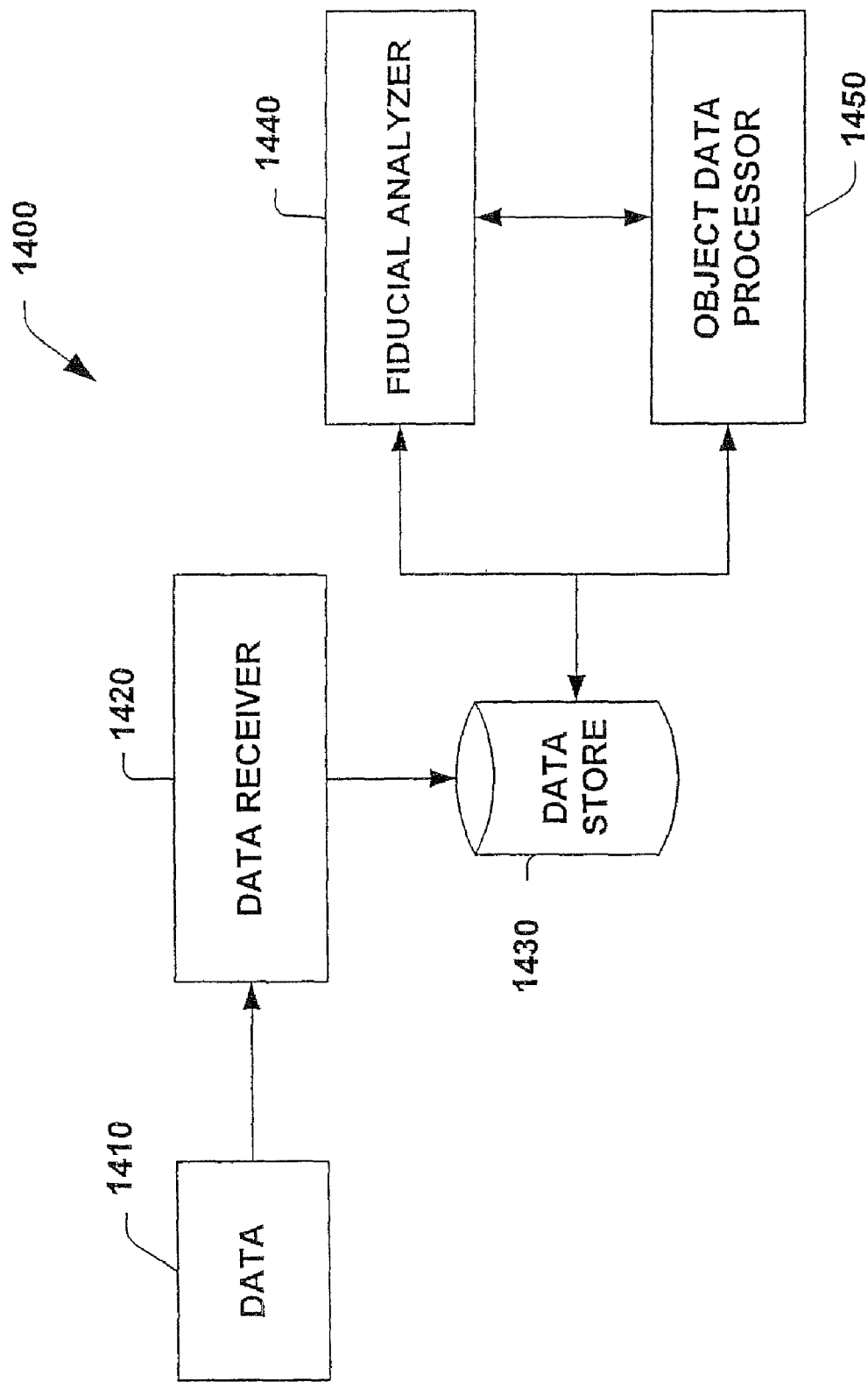
FIG. 14 is a schematic block diagram of an example system for improving the quality of an MRI image degraded by rotational motion during image acquisition.

FIG. 14 is a schematic block diagram of an example system 1400 for improving the image quality of an object where the image is degraded by rotational motion of the object during image acquisition. System 1400 includes a data receiver 1420 that receives an image data 1410 from the object. The data 1410 can include, but is not limited to, data concerning the object, and data associated with a fiducial associated with (e.g., marked on, attached to, located near, inserted in) the object. Data receiver 1420 stores the data in one or more data stores 1430. In one example, the image data is stored in one set of data stores while the fiducial data is stored in a second set of data stores. In another example, the object data and the fiducial data are stored together. Data store 1430 can be, for example, a disk, a tape, a memory (e.g., RAM), and so on. Data store 1430 can store the image data in data structures including, but not limited to, arrays, trees, lists, tables, and so on.

System 1400 includes a fiducial analyzer 1440 that determines a reference sinusoidal fiducial trajectory data from initial point source data. Furthermore, fiducial analyzer 1440 examines data from data store 1430 and computes an actual fiducial trajectory data. Fiducial analyzer 1440 then compares the reference sinusoidal fiducial trajectory data with the actual fiducial trajectory data and stores the result of the comparison.

System 1400 also includes an object data processor 1450 that selectively manipulates one or more pieces of object data stored in the data store 1430 to facilitate improving the quality of an image that was degraded by rotational motion during image acquisition. Object data processor 1450 undertakes this selective processing based, at least in part, on the comparison produced by fiducial analyzer 1440.

In one example of system 1400, data 1410 includes one or more projection data of radial k-space data acquired from an MRI device. In another example, data 1410 is a sinogram data. In one example of system 1400, data 1410 includes a fiducial data that is received from a high signal fiducial mark. The high signal fiducial mark can be, for example, a gadolinium filled tuned fiducial. Another example of system 1400 includes a low signal fiducial marker. Another example of system 1400 includes a fiducial data filter that removes the fiducial data from the image data to facilitate removing artifacts from a reconstructed image where the artifacts are associated with the fiducial.

Object data processor 1450 can, for example, manipulate object data to improve the quality of an image degraded during image acquisition by rotational motion by performing actions, including but not limited to, deleting projection data, relocating projection data in the data store 1430, and/or combining projection data. In general, the object data processor 1450 modifies the acquired image data so that the fiducial trajectory data more closely resembles or matches the reference trajectory data. Since system 1400 can produce corrected object data, an extension of system 1400 can include, for example, an image processor (not illustrated) that produces a viewable image of the object from the manipulated object data. Furthermore, an extension to system 1400 can include a signaler (not illustrated) that generates a control signal indicating that system 1400 desires one or more additional projection data from the radial k-space. When this additional data is acquired, a data integrator (not illustrated) can integrate the additionally acquired data with previously acquired corrected data. The integration can include, but is not limited to, replacing previously acquired data, averaging with previously corrected data, correcting previously acquired data, and so on. It is to be appreciated that data receiver 1420, fiducial analyzer 1440, object data processor 1450, the image processor, the signaler, and the data integrator, can be computer components as that term is described herein.

Example systems, methods, and objects described herein may be stored, for example, on a computer-readable media. Computer-readable media can include, but are not limited to, an application specific integrated circuit (ASIC), a compact disc (CD), a digital versatile disk (DVD), a random access memory (RAM), a read only memory (ROM), a programmable read only memory (PROM), a disk, a carrier wave, a memory stick, and so on.

Thus, an example computer-readable medium can store computer executable instructions for a computer implemented method for reducing the effects on image quality of rotational motion of an object during image acquisition. The method includes receiving a point source data associated with a fiducial associated with the object to be imaged and computing a point source location based on the point source data. The method includes computing a predicted sine wave data based on the point source location and/or the point source data. The method includes receiving an observed image data that has a set of projection data associated with the object to be imaged, and an observed waveform data associated with the predicted sine wave data. Once the observed image data is retrieved, the method compares the predicted sine wave data with the observed waveform data and selectively processes the observed image data to reduce the effects of rotational motion of the imaged object. The processing can include, but is not limited to, removing projection data, reordering projection data, and acquiring additional projection data.

Similarly, a computer-readable medium can store computer executable components of a system for improving the image quality of an object degraded by rotational motion of the object during image acquisition. The example system includes a data receiving component for receiving an image data from the object, where the image data includes object data and fiducial data. The example system also includes data stores for storing the object data and the fiducial data, either individually or collectively. The example system may also include a fiducial analyzer configured to determine a reference sinusoidal fiducial trajectory data and an actual fiducial trajectory data and to compare the two trajectory data. The example system may also include an object data processor configured to selectively manipulate object data to improve the quality of an object image degraded by rotational motion of the object based.

Figure 15:
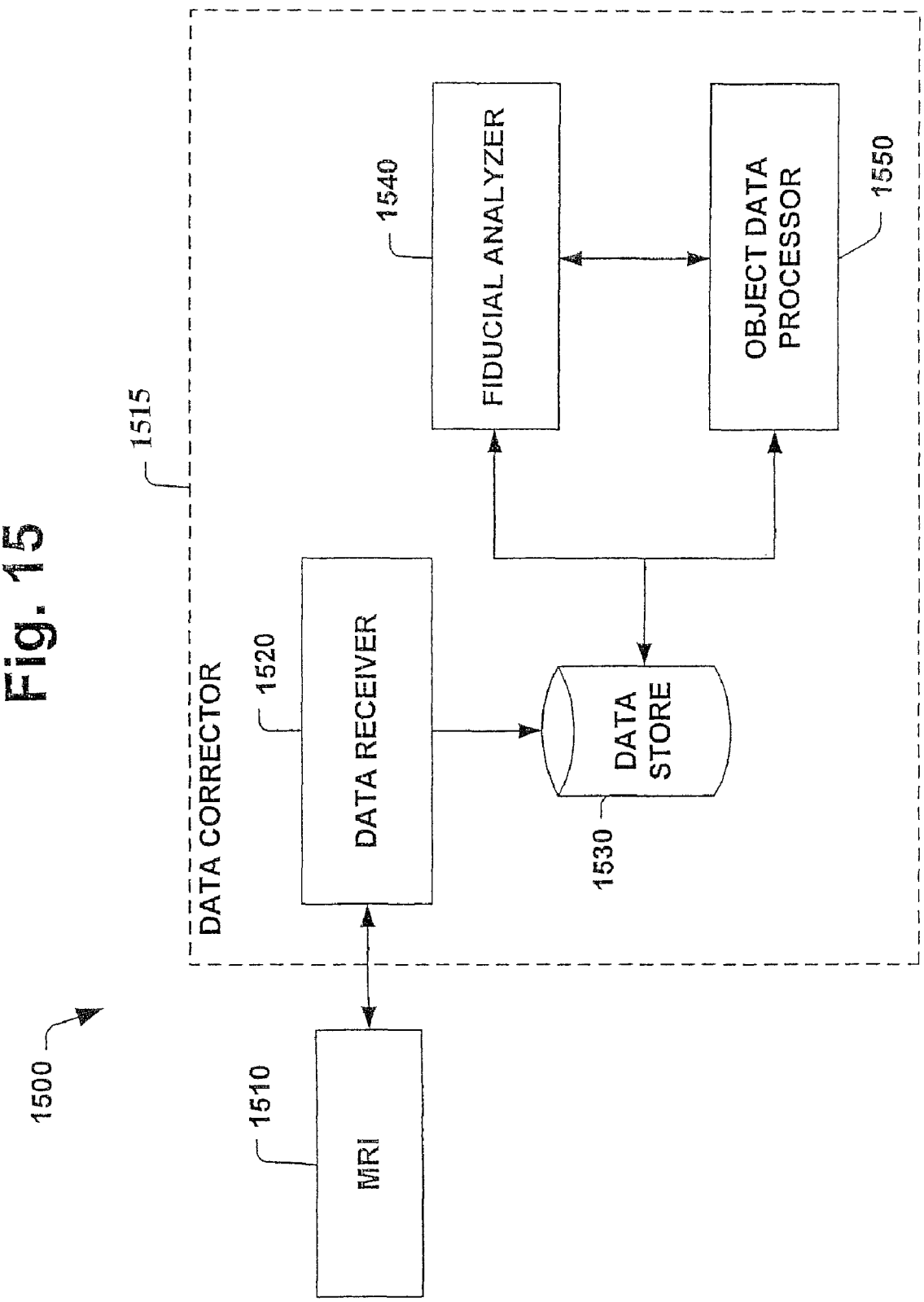
FIG. 15 illustrates an example MRI system interacting with a data corrector.

FIG. 15 illustrates an example system 1500 in which an MRI system 1510 interacts with a data corrector 1515. The data corrector 1515 can include, for example, a data receiver 1520, a data store 1530, a fiducial analyzer 1540, and an object data processor 1550, substantially similar to the computer components described in FIG. 14. The MRI system 1510 can be operably connected to the data receiver 1520 by for example, direct connections, local area network, wide area network, satellite communications, cellular communications, and so on.

Figure 16:
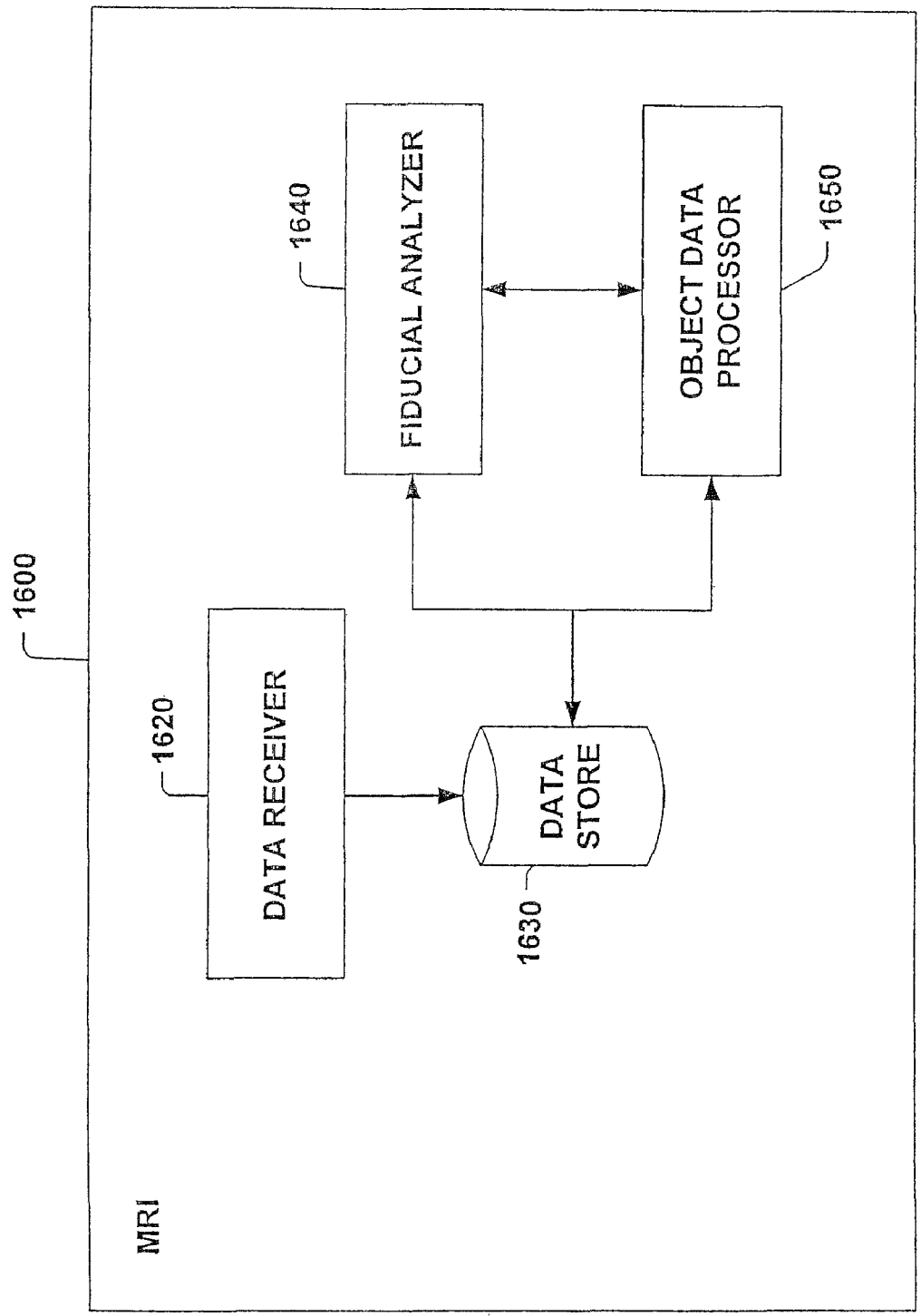
FIG. 16 illustrates an example MRI system that includes a data corrector.

FIG. 16 illustrates an example MRI system 1600 that includes computer components that faun a data corrector. The components of the data corrector include, but are not limited to, a data receiver 1620, a data store 1630, a fiducial analyzer 1640, and an object data processor 1650 that may be substantially similar to the computer components described above in connection with FIG. 14.

What has been described above includes several examples. It is, of course, not possible to describe every conceivable combination of components or methodologies for purposes of describing the methods, systems, computer readable media and so on employed in improving the quality of MRI images affected by rotational motion of the object being imaged. However, one of ordinary skill in the art may recognize that further combinations and permutations are possible. Accordingly, this application is intended to embrace alterations, modifications, and variations that fall within the scope of the appended claims. Furthermore, to the extent that the term "includes" is employed in the detailed description or the claims, it is intended to be inclusive in a manner similar to the term "comprising" as that term is interpreted when employed as a transitional word in a claim.

What is claimed is:

1. A non-transitory computer readable medium storing computer executable instructions operable to perform a method, the method comprising:

controlling an imaging apparatus to acquire an image from an object associated with a fiducial;

receiving a point source data associated with the fiducial, the point source data being acquired from a first projection data $S_1$ acquired at a first time $T_1$ from a first viewing angle $\theta_1$ resulting in a first projected distance $r_1$ and a second projection data $S_2$ acquired at a second time $T_2$ from a second viewing angle $\theta_2$ resulting in a second projected distance $r_2$;

computing a point source location based, at least in part, on the point source data, where computing the point source location comprises:

determining $R_{res}$, where $R_{res}$ is the displacement component of a polar coordinate for the point source; and determining $\theta_{res}$, where $\theta_{res}$ is the angular component of the polar coordinate for the point source;

computing a predicted waveform data based, at least in part, on one or more of the point source location, and the point source data;

receiving an observed image data comprising:

one or more projection data of a non-Cartesian k-space associated with the object; and an observed waveform data related to a location of the fiducial associated with the object and further associated with the predicted waveform data; and producing a selectively processed observed image data to reduce the effects of rotational motion of the object during image acquisition based, at least in part, on comparing the predicted waveform data and the observed waveform data.

2. The non-transitory computer-readable medium of claim 1, the imaging apparatus being one of, a magnetic resonance imaging (MRI) apparatus, an x-ray imaging apparatus, a positron emission tomography (PET) apparatus, a single photon emission computed tomography (SPECT) apparatus, and an optical light imaging apparatus.

3. The non-transitory computer-readable medium of claim 2, the method comprising computing an image of the object based on the selectively processed observed image data.

4. The non-transitory computer-readable medium of claim 1, the method comprising:

generating a signal to acquire one or more additional projection data;

providing the signal to the imaging apparatus to control the imaging apparatus;

receiving the additional projection data;

producing an updated observed waveform data based, at least in part, on the additional projection data; and selectively reprocessing the observed image data based, at least in part, on recomparing the predicted waveform data and the updated observed waveform data.

5. The non-transitory computer-readable medium of claim 1, where selectively processing the observed image data comprises one or more of, removing one or more projection data from the one or more projection data, reordering a projection data in the one or more projection data, and arithmetically combining one or more projection data.

6. The non-transitory computer-readable medium of claim 5, the method comprising repeating the actions of claim 1 until the predicted waveform data and the updated observed waveform data agree to within a pre-determined, configurable tolerance.

7. The non-transitory computer-readable medium of claim 6, the method comprising computing an image of the object based on the selectively processed observed image data.

8. A system, comprising:
a data receiver configured to receive an image data from an object associated with a fiducial, the image data comprising an object data and a fiducial data;
one or more data stores for storing the object data and the fiducial data;
a fiducial analyzer configured to determine a reference fiducial trajectory data, an actual fiducial trajectory data, and a comparison trajectory data that stores a result of comparing the reference fiducial trajectory data and the actual fiducial trajectory data; and
an object data processor configured to produce selectively manipulated object data and to improve the quality of an image where the image is degraded by rotational motion of the object during image acquisition.

9. The system of claim 8, the object data comprising projection data of a non-Cartesian k-space data acquired from an MRI device.

10. The system of claim 9, the fiducial data being received from a high signal gadolinium filled tuned fiducial apparatus.

11. The system of claim 10, the object data processor including a logic configured to delete one or more projection data, to relocate one or more projection data in the one or more data stores, and to combine one or more projection data.

12. The system of claim 11, including an image processor configured to produce a viewable image of the object from the selectively manipulated object data.

13. A system, comprising:
a magnetic resonance imager configured to acquire an MRI image; and
a data corrector configured to reduce the effects on an MRI image of rotational motion of an object associated with a fiducial marker, the rotational motion occurring during image acquisition:
the magnetic resonance imager comprising:
a polarizing magnetic field generator configured to generate a polarizing magnetic field in an examination region;
an RF generator configured to generate an excitation magnetic field that produces transverse magnetization in nuclei subjected to the polarizing magnetic field;
a sensor configured to sense a magnetic resonance signal produced by the transverse magnetization;
a gradient generator configured to generate a magnetic field gradient to impart a read component into the magnetic resonance signal, where the read component indicates a location of a transversely magnetized nuclei along a first projection axis, the gradient generator being configured to generate subsequent magnetic field gradients to impart subsequent read components into the magnetic resonance signal that indicates subsequent locations of the transversely magnetized nuclei along subsequent projection axes;
a pulse controller operably coupled to the RF generator, the gradient generator, and the sensor, the pulse controller being configured to conduct a scan in which a series of data points are acquired at read points along a non-Cartesian axis to form a magnetic resonance data view, subsequent magnetic resonance data views defining a magnetic resonance data set;
a data store configured to store the magnetic resonance data set; and
a processor configured to reconstruct an image array for a display from the stored magnetic resonance data set.

* * * * *